United States Patent
Greene et al.

(10) Patent No.: US 9,880,056 B2
(45) Date of Patent: Jan. 30, 2018

(54) SYSTEM AND METHOD FOR NON-DESTRUCTIVE, IN SITU, POSITIVE MATERIAL IDENTIFICATION OF A PIPE

(71) Applicant: TDW Delaware, Inc., Wilmington, DE (US)

(72) Inventors: Kenneth James Greene, Flagstaff, AZ (US); Chris Caraway, Bixby, OK (US); Gregory Donikowski, Owasso, OK (US); Joel Troyer, Tulsa, OK (US)

(73) Assignee: TDW Delaware, Inc., Wilmington, DE (US)

( * ) Notice: Subject to any disclaimer, the term of this patent is extended or adjusted under 35 U.S.C. 154(b) by 516 days.

(21) Appl. No.: 14/565,206

(22) Filed: Dec. 9, 2014

(65) Prior Publication Data

US 2015/0377707 A1 Dec. 31, 2015

Related U.S. Application Data

(60) Provisional application No. 62/017,964, filed on Jun. 27, 2014.

(51) Int. Cl.
*G01J 3/443* (2006.01)
*G01J 3/02* (2006.01)
(Continued)

(52) U.S. Cl.
CPC ............. *G01J 3/443* (2013.01); *G01J 3/0275* (2013.01); *G01N 3/42* (2013.01); *G01N 33/20* (2013.01);
(Continued)

(58) Field of Classification Search
CPC .......... G01J 3/443; G01J 3/0275; G01N 3/42; G01N 33/20; G01N 2203/0244; G01N 2203/0274; F16L 2201/60
(Continued)

(56) References Cited

U.S. PATENT DOCUMENTS 3,926,041 A 12/1975 Shaw
4,641,968 A 2/1987 Grandy
(Continued)

OTHER PUBLICATIONS

Use of Automated Ball Indentation Testing to Measure Flow Properties and Estimate Fracture Toughness in Metallic Materials, Fahmy M. Haggag et al. 1990, pp. 188-208.
(Continued)

*Primary Examiner* — Bo Fan
(74) *Attorney, Agent, or Firm* — Gable Gotwals

(57) ABSTRACT

A system and method for non-destructive, in situ, positive material identification of a pipe selects three test areas that are separated axially and circumferentially from one another and then polishes a portion of each test area. Within each polished area, a non-destructive test device is used to collect mechanical property data and another non-destructive test device is used to collect chemical property data. An overall mean for the mechanical property data, and for the chemical property data, is calculated using at least two data collection runs. The means are compared to a known material standard to determine, at a high level of confidence, ultimate yield strength and ultimate tensile strength within +/−10%, a carbon percentage within +/−25%, and a manganese percentage within +/−20% of a known material standard.

26 Claims, 3 Drawing Sheets

(51) Int. Cl.
*G01N 3/42* (2006.01)
*G01N 33/20* (2006.01)

(52) U.S. Cl.
CPC .. *F16L 2201/60* (2013.01); *G01N 2203/0244* (2013.01); *G01N 2203/0274* (2013.01)

(58) Field of Classification Search
USPC .............................................. 702/100; 701/1
See application file for complete search history.

(56) References Cited

U.S. PATENT DOCUMENTS

| | | | |
|---|---|---|---|
| 4,719,583 | A | 1/1988 | Takafuji et al. |
| 4,852,397 | A | 8/1989 | Haggag |
| 5,483,821 | A | 1/1996 | Mazzoleni et al. |
| 7,596,419 | B2 | 9/2009 | Fiore et al. |
| 7,839,969 | B2 | 11/2010 | Gallup et al. |
| 8,355,126 | B2 | 1/2013 | Goulter et al. |
| 8,436,991 | B2 | 5/2013 | Senac |
| 2009/0229349 | A1 | 9/2009 | Bowie |
| 2012/0137468 | A1 | 6/2012 | Bressendorff et al. |
| 2013/0195248 | A1 | 8/2013 | Rothschild et al. |
| 2014/0032012 | A1* | 1/2014 | Joshi ..................... G01S 13/865 701/1 |

OTHER PUBLICATIONS

An Update of ILI Tools & Other Industry Technologies, Lloyd Pirtle, Aug. 27, 2013.
Positive Material Identification-Handheld Niton XRF Analyzers, www.niton.com.
Automated Ball Indentation, Advanced Technology Corporation.
Sep. 2013 Meeting Presentation; Pipeliners Club of Tulsa.
Amen B: "In-situ analyses to characterize the properties and metallurgical attributes of in-service piping", NACE-International Corrosion Conference Series 2013, 2417, Mar. 17, 2013.

* cited by examiner

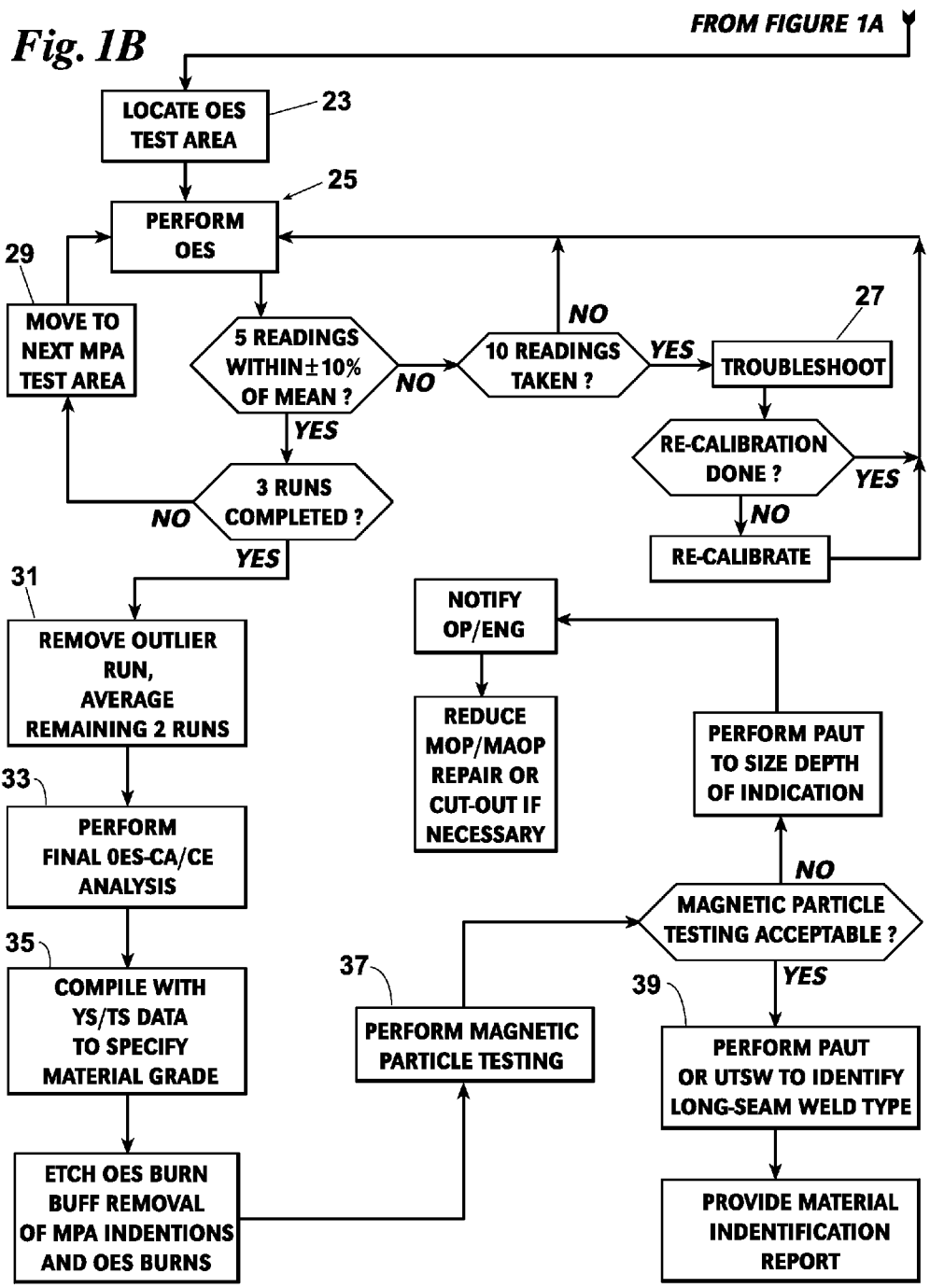

SYSTEM AND METHOD FOR NON-DESTRUCTIVE, IN SITU, POSITIVE MATERIAL IDENTIFICATION OF A PIPE

CROSS-REFERENCE TO CO-PENDING APPLICATIONS

This application claims the benefit of U.S. Prov. Pat. Appl. No. 62/017,964, titled System and Method for Non-Destructive, In-Situ, Positive Material Identification of a Pipe, filed Jun. 27, 2014.

BACKGROUND OF THE INVENTION

This invention relates generally to systems and methods used to identify and track the material used for each pipe of a pipeline. More specifically, the invention relates to non-destructive, on-site (in situ) systems and methods used to identify the material characteristics of the pipe.

Federal regulations require pipeline operators to identify and track the material used for each pipe which makes up their respective pipelines. The only way of doing this with any degree of certainty is to tap into the pipe and send the resulting coupon to a lab for analysis. The coupon is machined to ASTM standard specification and then pull-tested until yield (i.e., material memory is lost, coupon is elongated and cannot return to original size) and then beyond yield until failure occurs to determine tensile strength (see ASTM E8 tensile testing method). The current method is time consuming, costly, damages the pipe (which then must be repaired or fitted with a closure fitting), and is limited in that each pipe of the pipeline cannot be tested. Not only is there no non-destructive material identification system or method available, operators expect future regulations to require more precise material identification methods and shorter timelines for producing that material identification.

SUMMARY OF THE INVENTION

A system for non-destructive, in situ, positive material identification of a pipe, the pipe being part of a pipeline, the system including:
  means for identifying an appropriate test area on a surface of a pipe;
  non-destructive means for collecting mechanical property data from the test area;
  non-destructive means for collecting chemical property data from the test area;
  means for analyzing the collected mechanical and chemical property data; and
  means for comparing the analyzed mechanical and chemical property data to a known material standard;

The mechanical property data collection means provides, at 95% confidence level, data sufficient to determine ultimate yield strength and ultimate tensile strength at least within +/−10% of the known material standard. The chemical property data collection means provides, at an 85% confidence level, data sufficient to calculate a carbon percentage in a range of at least +/−25% and, at a 90% confidence level, a manganese percentage in a range of at least +/−20% of the known standard.

The system makes use of the following preferred method, with the size and number of test areas, number of readings, and the variances used to decide whether to keep or discard a reading or a run, are those found by the inventors to be the ones which reliably accomplish the system's intended purpose:

1. Selecting three test areas on the pipe, each 12 in.×6 in. (30.48 cm to 15.24 cm) and separated axially and circumferentially from the other test areas.
2. Within each test area, polishing a portion of test area, 1½ in×2½ in. area (3.81 cm.×6.35 cm), within which a mechanical properties assessment ("MPA" or "MPA Test") and a chemical analysis and carbon equivalency assessment ("CA/CE" or "CA/CE Test") takes place.
3. Within each polished area conducting an MPA Test in which a predetermined number of mechanical property readings are provided by a ball indenter, a minimum of five and a maximum of ten readings. These readings make up a run at the respective MPA Test location and provide yield strength/tensile strength ("YS/TS") averages.
4. Discarding a reading if the reading falls outside of a predetermined variance, ±5% of the mean, and taking an additional reading to replace it.
5. Producing a total of three MPA Test runs and discarding the run with the greatest variance from the average of all three runs.
6. Within each test area, selecting a CA/CE Test location adjacent to the MPA Test location.
7. Within each of the three CA/CE Test locations, using an optical emissions spectrometer ("OES") to provide a predetermined number readings for one or more chemical properties, a minimum of 5 and a maximum of 10 readings. Each reading records all of the elements listed in specification API-5L Table 4. These readings make up a run at the respective CA/CE Test location.
8. Discarding a reading if it falls outside of a predetermined variance, ±10% of the mean for carbon, and taking an additional reading to replace it.
9. Producing a total of three CA/CE runs and discarding the run with the greatest variance from the average of all three runs.
10. The YS/TS average and the CA/CE average for carbon and manganese are compared to a known material standard specification to determine the pipe material grade.

The objectives of this invention are to positively identify the key material properties of a pipe while the pipe is in-situ and do so without degrading the integrity of the pipe in any way.

BRIEF DESCRIPTION OF THE DRAWINGS

FIG. 1B is a process flow diagram which continues from FIG. 1A. The flow diagram covers the chemical analysis ("CA") and carbon equivalency ("CE") assessment portion of the system and method.

DETAILED DESCRIPTION OF THE PREFERRED EMBODIMENTS

Figure 1A:
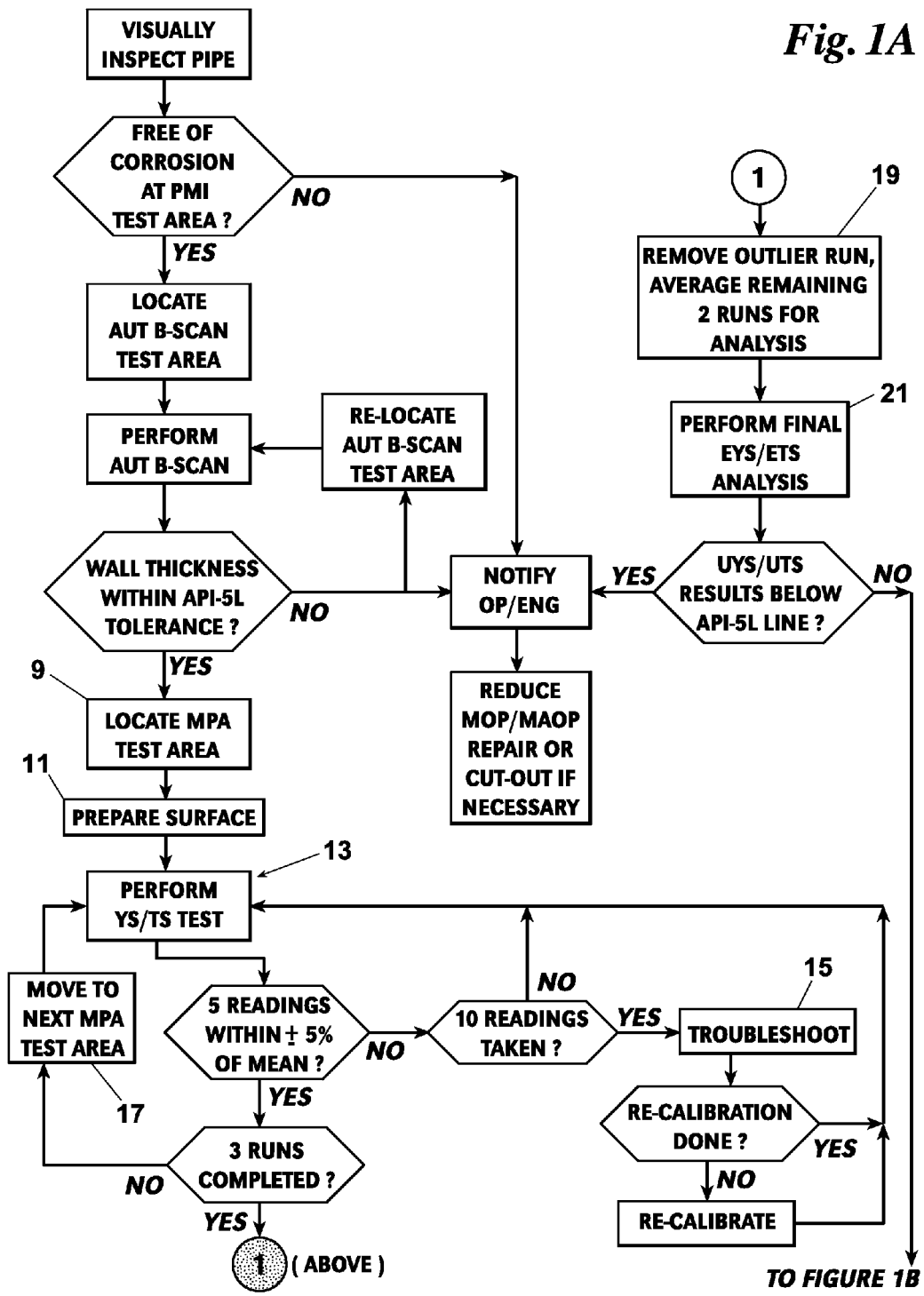
FIG. 1A is process flow diagram of a preferred embodiment of the system and method of this invention. The flow diagram covers the mechanical properties assessment ("MPA" or "MPA Test") portion of the system and method which includes a yield strength/tensile strength ("YS/TS Test").

The system and method described here provide non-destructive material property values only available through destructive testing of a test specimen removed from the material in question and tested at an off-site laboratory. The term, non-destructive testing technique, as used in the context of this patent application means a testing technique that does not require cutting into and removing a portion of the pipe to obtain a test specimen of the pipe and one that is not detrimental to the integrity of the pipe.

The system and method, which apply to the pipe when in-service (i.e., on site, part of a pipeline, and in situ) and provide positive material identification ("PMI") of the pipe, include a mechanical properties assessment ("MPA" or "MPA Test") and a chemical analysis and carbon equivalency assessment ("CA/CE" or "CA/CE Test"). The MPA uses yield and tensile strength test ("YS/TS Test") technology, preferably a mobile means for collecting yield and tensile strength data. The CA/CE assessment uses optical emissions spectrometry ("OES") technology, preferably a mobile means for collecting constituent component data.

When the system and method are followed, the following accuracy tolerances are achieved:

Ultimate yield strength ("UYS") +/−10% at a 95% confidence level

Ultimate tensile strength ("UTS") +/−10% at a 95% confidence level

Carbon percentage ("C") +/−25% at a 85% confidence level

Manganese percentage ("Mn") +/−20% at a 90% confidence level

These tolerances were calculated by conducting a validation process using a third party testing laboratory as the standard. The system and method were applied and validated on over 30 samples and the results were compared to the test lab results. The UYS and UTS tolerances are relative to a value. The C and Mn tolerances are relative to a percentage (e.g., +/−25% of 0.25% C).

Prior to performing the method in the field, material sample reference standards should be provided to the field technicians or the system should be calibrated prior to use. The sample reference standards should be of a like material type, grade and wall thickness as expected to be encountered in the field and have a reasonable tolerance for unknown or unidentifiable materials.

Certain conditions can negatively affect the performance of the system and method or prevent it from being completed. These conditions include:

circumstances with the excavation or ditch preparation that prevents the safe use of the equipment or poses a threat to the field technician;

external corrosion that prevents an acceptable test area from being located or corrosion that may alter the test results;

internal metal loss falling outside of API-5L tolerances;

ultimate yield strength falling outside the range recorded specifications;

chemical analysis or CE that is outside the range of recorded specifications; and magnetic particle surface indications that might propagate, or already have propagated, into surface cracks.

In a preferred embodiment of the system and method, an ultrasonic scan is performed to ensure each area or location identified for testing is free from laminations or severe internal pitting. Three test areas are selected, with each test area spaced axially and circumferentially from the other test areas. The YS/TS Test is then performed within each test area to determine yield and tensile strength. Chemical analysis and CE test ("CA/CE Test") is then done within each test area to determine the chemical constituent makeup of the pipe (primarily C and Mn) and the respective percentages. Finally, each test area is magnetic particle inspected to ensure the integrity of the test surface. If the testing process has been found detrimental to the pipe in some way, such as but not limited to a surface-breaking crack, then the test is deemed to have been a destructive one rather than non-destructive.

At the start of the method, the pipe section to-be-tested may have to be excavated and exposed (if not already exposed or above ground). Any excavation should be done in such a way as to provide a safe working environment for test personnel when conducting the method.

Next, three test areas are selected. The reason for multiple test areas is that the pipe may have non-homogeneous areas, spots or locations and, therefore, no one area, spot or location may be an accurate representation of the overall pipe. Each potential test area preferably measures 12 in. (30.48 cm) long (axial direction) and 6 in. (15.24 cm) wide (circumferential direction) is selected. One or more of the three areas may have to change in size if pipe conditions or circumstances dictate a different sized test area. Ideally, the three test areas are separated from one another axially and circumferentially (e.g., one at the 12 o'clock position, one at the 9 or 10 o'clock position, and another at the 2 or 3 o'clock position). The areas can be adjacent to one another.

Because external pitting produces false readings to the YS/TS Test, the test area is visually inspected for corrosion. If corrosion is seen, operations and engineering should be notified so that corrective action, if required, can take place. Corrective action may include reducing the maximum operating pressure ("MOP") and maximum allowable operating pressure ("MAOP"), repairing the pipe, or cutting out and replacing a section of the pipe (or the entire pipe) as necessary.

If the test area is free of corrosion, the pipe is scanned to determine whether its wall thickness falls within API-5L (Table 11) tolerance limits. A scanner suitable for this is an AUT Solutions (Fulshear, Tex.) B-scanner or its equivalent.

If the wall thickness falls below the API-5L tolerance limits—for example, because of an internal mill anomaly or metal loss—operations and engineering should be notified so that appropriate corrective action can be taken. Regardless, whenever an anomaly or metal loss is detected, the YS/TS Test should be performed at an area located at least 3 in. (7.62 cm) away from the anomaly or loss. If that is not possible, then another test area may need to be selected with the above steps repeated.

After the scan is completed, the test area should be verified free of laminations and internal pitting and not over a long-seam weld.

Next, because the pipe is typically coated and may have other surface imperfections, and because the CA/CE Test requires a bare metal surface, the surface of the test area should be prepared by polishing. This can be accomplished by an electric or pneumatic grinder using successively finer polishing media. The goal is to create a pit-free test area having a near-mirror like finish within each of the 12 in.×6 in. (30.48 cm to 15.24 cm) test areas.

Typically, about a 3 ft. (0.914 m) long area of the coating is removed. Within each of the three 12 in.×6 in. (30.48 cm×15.24 cm) test areas, a 2 in.×3 in. (5.08 cm×7.62 cm) prep area is polished, with the final stages of polishing staying within an area of 1½ in.×2½ in. (3.81 cm.×6.35 cm) so as to not go beyond the prep area and bring any loose material back into that area. Preferably, the final polishing stage is in an area even smaller, 1 in.×2 in (2.54 cm×5.08 cm).

Each run of the YS/TS Test is performed on the polished test area surface using a test device having a ball indenter, with the first run being done in the first 12 in.×6 in. (30.48×15.24 cm) test area and the second and third runs being done in the other test areas, respectively. More specifically, each run is done within the small polished area within each test area described above. The same is true of the CA/CE Test and its runs described later on.

A test device suitable for this test is a Frontics (Seoul, KR) AIS 2100 non-destructive tensile property tester or its equivalent. Although this type of tensile testing is a non-destructive testing technique relative to the prior art method, it is not recognized under industrial codes such as SNT-TC-1A as being an actual non-destructive technique.

During the original calibration of the test device, or during any re-standardization or re-calibration of it, the analyzed calibration test data readings are required to be within +/−5% of the mean. The analysis is preferably done by way of a software-based algorithm of the load/depth cycles and of stress/strain and which makes use of known material property relationships. The tolerances for the actual field test EYS/ETS (elastic) results are specified to be within +/−10% of the actual test specimen's material properties. These tolerances should be understood and agreed upon prior to using the MPA method.

What has been found to be critical in obtaining tight tolerances is tight control over the testing conditions and processes. Sloppy surface preparation or sloppy test procedures (or both) can lead to highly variable and inaccurate results. Therefore, the system and method includes controls to ensure that accurate data is being collected.

The YS/TS test device measures and adjusts the load as necessary to achieve a final predetermined fixed depth (e.g., a fixed depth of 0.006 in. or 0.0152 cm) throughout the predetermined number of load/depth measurement cycles. For example, the load could be about 50 g (0.050 kg) of force. Once the last and final load is applied, the resulting stress/strain data is analyzed by software means (using known physical relationships) to determine the EYS and ETS of that location.

Referring to FIG. 1A, at least three test areas are selected (see step 9) and YS/TS Test location within each of the test areas is polished as described above (see step 11). At each test location, a predetermined number of readings—a minimum of five readings and a maximum of ten readings—are taken with the YS/TS test device (see step 13). In a preferred embodiment, each reading represents a data point and is collected by sequentially applying the load a predetermined number of times (e.g., preferably 15 times) to achieve a final predetermined depth (e.g., exactly 0.006 in. or 0.0152 cm). The five readings are averaged and any reading that is not within a predetermined variance, +/−5% of the mean, is discarded. Each set of five readings constitutes a run.

If a reading is discarded, a new reading is taken—e.g., by sequentially applying the load the predetermined number of times to achieve the final predetermined depth—and a new five-reading average is calculated. This process of reading, re-calculating the average, and discarding a reading (if necessary) continues until five readings have been obtained which are within +/−5% of the mean. However, if ten readings have been taken and there are still not at least five readings within +/−5% of the mean, then troubleshooting should be performed and, if necessary, the test device should be re-standardized or re-calibrated. Standardization or calibration should be done using a known API-5L specimen.

Figure 2:
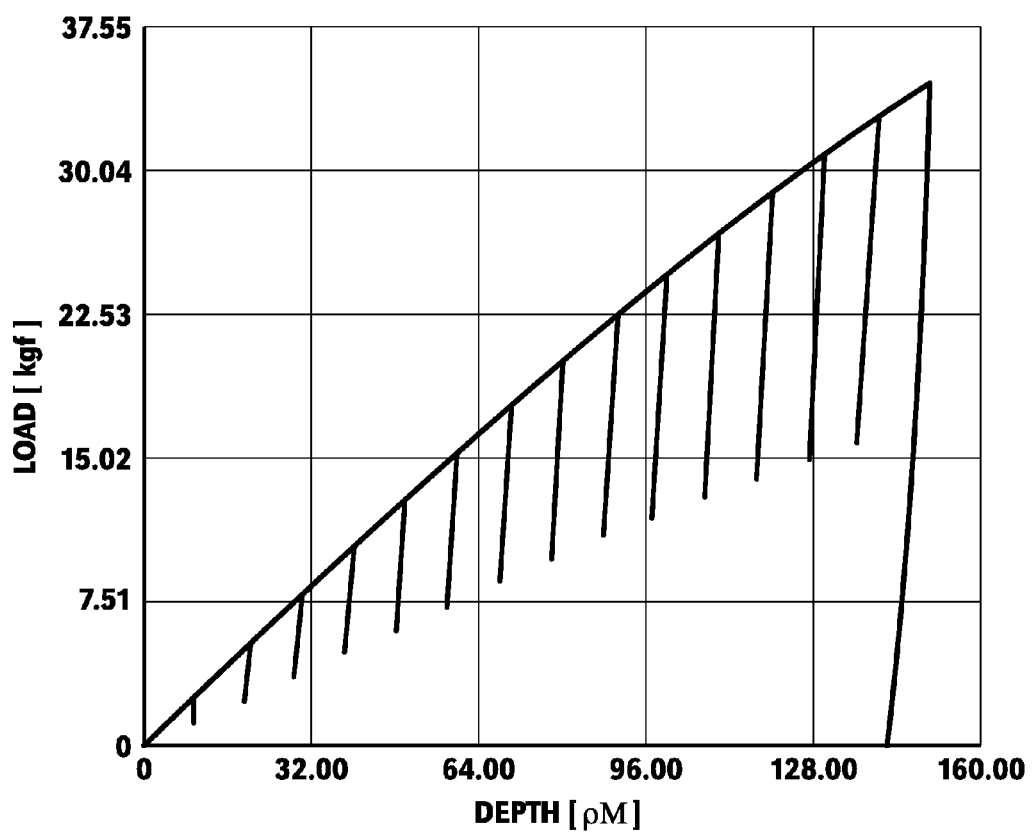
FIG. 2 is a graph showing the data collected during one reading of the YS/TS Test and having no errors in the data collection. Graphs that differ in appearance from this generally indicate some type of data collection problem.

When troubleshooting is being performed (see step 15), comparing a graph of actual results with that of a normal or expected graph of results (see FIG. 2) can help pinpoint a problem. The ball indenter could be bad, loose, interfered with by contaminants, or experiencing uneven stress or external shock; there could be a communication error with the supporting computer hardware; or poor data collection methods may have been used. For example, the test device could have been located at a long-seam weld or a heat-affected zone of the pipe. Each of these problems tend to produce their own characteristic graph which will differ in appearance from that of FIG. 2.

Once a minimum of five readings are taken which are within +/−5% of the mean, the YS/TS test device should be moved to the next MPA test area to collect another set of five good readings (minimum) (see step 17). The process used to collect the five good readings is the same as that used in the first location. Once five good readings have been collected, the test device should be moved once again, this time to the third MPA test area or location.

After five good readings have been collected at the third location (i.e., the third run), the results are evaluated to identify the outlier run (see step 19). The outlier dataset or run is defined as the dataset with the greatest variance from the mean of the three runs or data sets. The outlier run is then removed and the remaining two runs are averaged to determine EYS and ETS and UYS and UTS (see step 21).

Next, the CA/CE Test is performed using OES technology. A device suitable for this test is an Oxford Instruments (Abingdon, Oxfordshire, UK) PMI-MASTER Pro mobile unit or ARC-MET 8000 alloy analyzer unit or their equivalent. Although OES technology is a non-destructive technique relative to the prior art method, it is not recognized under industrial codes such as SNT-TC-1A as being an actual non-destructive technique.

The CA/CE test device creates a spark or non-destructive burn which vaporizes material. Light is then passed through the material vapor emissions, and the material component concentrations—in particular, C and Mn—are measured and analyzed. Software means compare the material component concentrations with API-5L material component charts and specifications for various material grade requirements. For the pipe to qualify as a specific material grade, in this system and method five or more readings must comply with that specific material grade's specification (the API-5L dictates nine chemical constituents that must be within a given tolerance as listed in API-5L-Table 4 before grade match can be certified.)

Referring to FIG. 1B, three different CA/CE Test locations are selected, with each location corresponding to one of the MPA Test locations within the three polished test areas (see step 23). At each location, a predetermined number of readings—a minimum of five readings and a maximum of ten readings—is taken with the OES test device (see step 25). The readings should be taken adjacent to the indentation from the YS/TS Test in that area. The five readings are averaged and any reading that is not within +/−10% of the mean for carbon is discarded.

If a reading is discarded, a new reading is taken and a new five-reading average is calculated. This process of reading, re-calculating the average, and discarding a reading (if necessary) continues until five readings have been obtained which are within a predetermined variance of the mean for carbon, +/−10% of the mean for carbon. However, if after ten readings there are not at least five readings within +/−10% of the mean, then troubleshooting should be performed (see step 27) and the test device might have to be re-standardized or re-calibrated.

Standardization or calibration should be performed on a known API-5L test specimen or manufacturer-provided standardization block. During this process (or during the original calibration process), the analyzed calibration test data readings must properly identify the test specimen. If ten data readings are taken without a proper identification being made, then troubleshooting should be performed.

Troubleshooting includes, but is not limited to, checking for power to the test device and determining whether there is no arc or an improper arc. Note that if ten data points are taken without five readings being within +/−10% of the mean for carbon, and it has been verified that the data collection area is not at a long-seam weld nor at a heat affected zone, then the area is assumed non-homogenous and the test location should be relocated elsewhere on the same component (for example, but not limited to, joint, fitting, valve, flange).

If successful results have been obtained during the first location, then the CA/CE test device is moved to a second location (see step 29). The process used to collect five good readings at the second location is the same as that used in the first location. Once five good readings have been collected here, the test device should be moved once again, this time to a third location.

After the run at each location are completed (i.e., a minimum of five good readings collected at each of the three locations), the results are evaluated to identify the outlier run (see step 31).

The outlier data set or run is the dataset with the greatest variance from the mean of the three runs or data sets. This culling of the data set uses C, Mn, or both as the primary elements for determining the outlier dataset. The outlier run is then removed and the remaining two runs are averaged to determine the C and Mn contents of the pipe. The tolerances for the constituent percentages in this system and method are specified to be within +/−25% of C and within +/−20% of Mn of actual test specimen material properties. These tolerances should be understood and agreed upon prior to using the CA/CE Test method.

The EYS/ETS results from the MPA Test (see step 21) and the CA/CE results from the CA/CE Test (see step 33) are used to specify the material grade (see step 35). Indentations from the YS/TS Test should be removed by buffing those locations. Burns from the CA/CE Test can be removed buffing. Burn removal can be verified using a nital etch.

The polished test area now should be non-destructively tested for surface breaking anomalies using magnetic particle testing (see step 37). A device suitable for this is a B-300 Series hand-held AC yoke (Parker Research Corp., Clearwater, Fla.).

If the test results are acceptable, phased array ultrasonic testing should be performed to identify the long-seam weld type: electric resistance welded ("ERW") or electric resistance lap welded (see step 39). A device suitable for this is an OmniScan MX2 ultrasonic flaw detector (Olympus Corp., Center Valley, Pa.) or its equivalent. If the results are not acceptable, phased array ultrasonic testing should be performed to size the depth of the indication (e.g., the depth of a surface-breaking crack) and operations and engineering should be notified so that appropriate corrective action can be taken.

The size and number of test areas, number of readings, and the variances used to decide whether to keep or discard a reading or a run, are those found by the inventors to be the ones which reliably accomplish the system's intended purpose. Tests conducted by the inventors have demonstrated that the system and method can positively identify pipe grades listed in Table 6 of API-5L from L390 up to X56. The system and method can be adapted for identifying pipe grade from L485 up to X70.

The preferred embodiments described above may not be all possible embodiments of the invention. The invention is defined by the following claims, and the claims include elements equivalent to those specifically recited in the claims.

What is claimed:

1. A method for non-destructive, in situ, positive material identification of a pipe, the method comprising:
   using an ultrasonic scanner on a surface of the pipe to collect wall thickness data;
   comparing the wall thickness data to a known API wall thickness tolerance limit;
   selecting at least three test areas on the surface of the pipe, the pipe being in-situ and part of a pipeline, each test area being separated axially and circumferentially from one another;
   polishing using a grinder and successively finer polishing media the surface of the pipe to a pit-free, near-mirrorlike finish within at least a portion of each test area;
   selecting a mechanical properties test location within the polished portion of each test area;
   using a tensile property tester having a ball indenter to collect a predetermined number of mechanical property data readings of the pipe at each mechanical properties test location, the predetermined number of mechanical property data readings representing a mechanical property data collection run;
   calculating a mean of the mechanical property data collection run;
   selecting a chemical properties test location within the polished area of each test area, each chemical properties test location being adjacent to a respective mechanical properties test location;
   using an optical emissions spectrometer to collect a predetermined number of chemical property data readings of the pipe at each chemical properties test location, the predetermined number of chemical property data readings representing a chemical property data collection run;
   calculating a mean of the chemical property data collection run;
   calculating an overall mean of the mechanical property data collection runs and of the chemical property data collection runs, each overall mean being calculated using at least two of its respective data collection runs;
   identifying a material of the pipe by comparing each overall mean to a known API material standard.

2. A method according to claim 1 wherein the predetermined number of mechanical property data readings and of chemical property data readings is a minimum of five and a maximum of ten readings.

3. A method according to claim 1 wherein any reading not within a predetermined variance from the calculated mean of a respective mechanical or chemical property data collection run is discarded.

4. A method according to claim 3 wherein the predetermined variance is ±5% from the calculated mean.

5. A method according to claim 3 wherein the predetermined variance is ±10% from the calculated mean.

6. A method according to claim 3 wherein an additional reading replaces the discarded reading.

7. A method according to claim 1 wherein the at least two of the data collection runs used to calculate the overall calculated mean for the mechanical or chemical property does not include an outlier data collection run.

8. A method according to claim 1 wherein the outlier data collection run is a data collection run having a calculated mean with the greatest variance from an overall calculated mean for the at least three data collection runs for the mechanical or chemical property.

9. A method according to claim 1 wherein the method provides, at 95% confidence level, mechanical property data sufficient to determine ultimate yield strength and ultimate tensile strength at least within +/−10% of the known API material standard.

10. A method according to claim 1 wherein method provides, at an 85% confidence level, chemical property data sufficient to calculate a carbon percentage in a range of at least +/−25% to the known API material standard.

11. A method according to claim 1 wherein the method provides, at a 90% confidence level, chemical property data sufficient to calculate a manganese percentage in a range of at least +/−20% to the known API material standard.

12. A system for non-destructive, in situ, positive material identification of a pipe which is part of a pipeline, the system comprising:
  at least three test areas on a surface of a pipe when in-situ, each test area being separated axially and circumferentially from one another and having a portion polished by a grinder with successively finer polishing media to a pit-free, near-mirrorlike finish;
  a tensile property tester having a ball indenter for collecting mechanical property data of the pipe from a mechanical properties test location within the polished portion of each test area, the tensile property tester providing a predetermined number of readings for a mechanical property at the mechanical properties test location, the predetermined number of readings constituting a mechanical property data collection run and being used to calculate a mean for the mechanical property data collection run; and
  an optical emission spectrometer for collecting chemical property data of the pipe from a chemical properties test location within the polished area of each test area, each chemical properties test location being adjacent to a respective mechanical properties test location, the optical emission spectrometer providing a predetermined number of readings for a chemical property at the chemical properties test location, the predetermined number of readings constituting a chemical property data collection run and being used to calculate a mean for the chemical property data collection run;
  wherein an overall calculated mean for at least two of the mechanical property data collection runs including mechanical data results of the pipe and an overall calculated mean for at least two of the chemical property data collection runs including chemical data results of the pipe is compared to a known API material standard.

13. A system according to claim 12 wherein the predetermined number of readings for the mechanical and chemical property data collection runs is a minimum of five and a maximum of ten readings.

14. A system according to claim 12 wherein a reading not within a predetermined variance from the calculated mean of its respective data collection run is discarded.

15. A system according to claim 14 wherein the predetermined variance is ±5%.

16. A system according to claim 14 wherein the predetermined variance is ±10%.

17. A system according to claim 14 wherein an additional reading replaces the discarded reading.

18. A system according to claim 12 wherein the at least two of the data collection runs used to calculate the overall calculated mean for the mechanical or chemical property does not include an outlier data collection run.

19. A system according to claim 18 wherein the outlier data collection run is a data collection run having a calculated mean with the greatest variance from an overall calculated mean for the at least three data collection runs for the mechanical or chemical property.

20. A system according to claim 12 wherein the system provides, at a 95% confidence level, data sufficient to determine ultimate yield strength and ultimate tensile strength at least within +/−10% of the known API material standard.

21. A system according to claim 12 wherein the system provides, at an 85% confidence level, chemical property data sufficient to calculate a carbon percentage in a range of at least +/−25% to the known API material standard.

22. A system according to claim 11 wherein the system provides, at a 90% confidence level, a manganese percentage in a range of at least +/−20% to the known API material standard.

23. A method according to claim 1 further comprising:
  buffing to remove any indentations made on the pipe by the ball indenter within the polished portion of each test area; and
  etching to remove any burns on the pipe caused by the optical emissions spectrometer within the polished portion of each test area.

24. A method according to claim 1 further comprising: using a magnetic particle tester on the pipe within the polished portion of each test area to determine a presence of a surface breaking anomaly on the pipe.

25. A method according to claim 24 further comprising using an ultrasonic flaw detector within the polished portion of each test area to identify a long-seam weld type selected from the group consisting of an electric resistance weld and an electric resistance lap weld.

26. A method according to claim 24 further comprising performing phased-array ultrasonic testing to determine a depth of the surface breaking anomaly.

* * * * *